United States Patent [19]

Glaunsinger et al.

[11] Patent Number: 5,466,605
[45] Date of Patent: Nov. 14, 1995

[54] METHOD FOR DETECTION OF CHEMICAL COMPONENTS

[75] Inventors: William Glaunsinger, Chandler; Ian Sorensen, Phoenix; Qingcheng Bao, Tempe; Michael J. McKelvy, Mesa, all of Ariz.

[73] Assignee: Arizona Board of Regents, Tempe, Ariz.

[21] Appl. No.: 31,610

[22] Filed: Mar. 15, 1993

[51] Int. Cl.⁶ .................................................... G01N 27/12
[52] U.S. Cl. .............. 436/6; 436/101; 436/124; 436/151
[58] Field of Search ................... 422/88, 90, 83, 422/98, 53, 82.02; 436/101, 124, 151, 152, 2, 3, 6; 338/34

[56] References Cited

U.S. PATENT DOCUMENTS

| | | | |
|---|---|---|---|
| 3,124,771 | 3/1964 | Rohrback | 422/53 X |
| 3,578,409 | 5/1971 | Silverman et al. | 436/151 X |
| 3,714,562 | 1/1973 | McNerney | 324/65 R |
| 3,888,110 | 6/1975 | Clark | 73/27 |
| 3,973,192 | 8/1976 | Justi et al. | 324/65 R |
| 4,196,427 | 1/1978 | Rudberg | 340/634 |
| 4,224,280 | 7/1978 | Takahama et al. | 422/98 |
| 4,343,768 | 8/1982 | Kimura | 422/98 X |
| 4,587,104 | 12/1983 | Yannopoulos | 422/94 |
| 4,592,967 | 2/1984 | Komatsu et al. | 428/697 |
| 4,839,767 | 6/1989 | Yoshioka et al. | 361/42 |
| 4,938,928 | 7/1990 | Koda et al. | 422/98 |
| 5,010,021 | 4/1991 | Bell et al. | 436/120 |
| 5,087,574 | 2/1992 | Bell et al. | 436/120 |
| 5,145,645 | 9/1992 | Zakin et al. | 422/98 |
| 5,208,162 | 5/1993 | Osborne et al. | 436/151 X |
| 5,243,238 | 9/1993 | Kean . | |

FOREIGN PATENT DOCUMENTS

| | | | |
|---|---|---|---|
| 90/15323 | 6/1989 | WIPO | G01N 27/407 |

OTHER PUBLICATIONS

McNerney, J. J., Buseck, P. R., *Science*, 178:611–612, Nov. 10, 1972.

*Primary Examiner*—Jeffrey R. Snay
*Attorney, Agent, or Firm*—David G. Rosenbaum

[57] ABSTRACT

A chemical switch device and method of sensing the presence of a chemical constituent in an ambient environment, the chemical switch device comprising a film which irreversibly reacts upon exposure to specific chemical components in the environment under the conditions of measurement. The reactions can lead to large changes in the physical and chemical properties of the film which are measurable electrically, optically or by other methods.

10 Claims, 3 Drawing Sheets

METHOD FOR DETECTION OF CHEMICAL COMPONENTS

BACKGROUND OF THE INVENTION

The present invention relates generally to a device and method for detection of specific chemical components in an environment containing many distinct chemical species. More particularly, the present invention relates to a chemical switch device comprising a film which irreversibly reacts upon exposure to specific chemical components in the environment under the conditions of measurement. The reactions can lead to large changes in the physical and chemical properties of the film which are measurable electrically, optically or by other methods. The term "conditions of measurement" is intended to mean any environmental conditions under which a reacted or unreacted state of the device can be determined. The chemical switches are "yes-no," intrinsically binary devices that can be miniaturized, mass produced and directly incorporated into digital electronic circuits.

Typically, electrical switches, such as fuses, are used to provide a break in an electrical circuit to prevent an electrical overload. Conventional irreversible switches are thermal fuses which fail by physical breakage of the electrical path due to resistive overheating. In the electrical embodiment of the present invention, an irreversible chemical switch can exhibit a large change in physical or chemical properties upon reaction of the switch material with a specific chemical component. The apparent physical or chemical change can manifest itself as a measurable increase or decrease of resistance due to an irreversible change in the switch material from a conductor or resistor to a resistor or conductor, respectively, upon reaction with a specific chemical component. The change is irreversible under the conditions of measurement, much like a conventional electrical fuse, except that the resistance of the irreversible chemical switch can either increase or decrease upon exposure to specific chemical components. Furthermore, other properties of the device, such as optical or thermal properties, can be used to monitor the extent of the irreversible reactions. The present invention also provides methods for detection of individual chemical components, e.g., hazardous gases, in an environment using an irreversible chemical switch.

The concept of an irreversible chemical switch, based upon irreversible chemical reactions, is believed to be heretofore unknown. In contradistinction to electrical fuses, which fail by thermal breakage of a conductive element, electrical irreversible chemical switches fail upon selective reaction of a conductive or resistive material with a chemical species; with failure being indicated by an increase or decrease in resistivity of the conductive or resistive material. The reaction between the conductive or resistive material and the chemical species causes an irreversible phase change in the conductive or resistive material as the chemical species to be detected forms a new phase, such as an alloy, amalgam or a corrosion product. The phase change creates a region or zone, propagated through the bulk of the chemical switch, which causes an abrupt change in the electrical resistance, electrical conductivity or other properties of the switch material. Optimally, the rate of change in electrical or other properties is rapid and has a sufficient magnitude to provide a reliable and measurable indication of the presence of specific chemical components.

An important aspect of the invention is the incorporation of highly durable materials as a selectively reactive element for the conductive or resistive material. These materials should be capable of being engineered in thin or thick-film form as the switch materials. For example, noble metals, either in substantially pure form, or as alloys with other noble metals, are very robust, being highly chemically inert, yet can be engineered for specific chemical reactivity. It is known from the prior art, however, that some noble metals undergo reversible surface reactions with certain chemicals when heated. Noble metal thin films (films of less than approximately 10,000 Å thickness), operating on the basis of surface reactions, have been used as chemical sensors for a limited number of chemical species. Another large class of chemical sensors, metal oxide semiconductor materials, are typically heated to between 300° C. and 1000° C. to facilitate adsorption and desorption of the chemical species on the semiconductor material. Changes in resistivity of the semiconductor material are measured to determine the presence or absence of the chemical species.

Gold thin films have been used to detect the presence of mercury vapor. McNerney, J. J., et al., Mercury Detection by Means of Thin Gold Films, *Science* 178:611–612 (1972) disclosed detection of mercury vapor by linear changes in resistivity in gold thin films having thicknesses of 75 Å and 400 Å, with sheet resistivities of 2 to 10 ohms, respectively. McNerney, et al. suggest that the effects of adsorbed mercury atoms on the conductivity of gold films is a surface effect rather than a bulk alloy effect. U.S. Pat. No. 3,714,562 to McNerney, issued in 1973, (hereinafter "McNerney '562") disclosed that thin film gold layers, having a film thickness of between 75 and 1,000 Å, preferably between 75 and 300 Å, undergo resistivity changes upon exposure to mercury vapor. The patent contemplates that other thin film metals may be used to detect the presence of other chemicals to which the metal has a chemical affinity. For example, the patent teaches that silver may be used to detect iodine.

The McNerney '562 patent further teaches that if thicker metal films are used, the resistance change becomes masked by the properties of the bulk material. It is taught that the thin films referred to have a mean free path for electrons which is significantly reduced when a contaminant chemical species is adsorbed onto the film. It was found that upon exposure to mercury vapor, the gold thin film exhibited immediate increases in resistance. Over time, the rate of change in resistance increased slowly, which was believed due to amalgamation of mercury with the gold; a reaction that can be reversed by heating the gold.

The sensor described in the McNerney '562 patent consists of a glass plate substrate on which a thin layer of gold has been deposited. The gold layer is configured to provide a reasonably large surface area of gold and a reasonably long resistance path between electrical terminals.

McNerney '562 recognized that the resistance change in the molecular thickness thin film is a function of concentration of the vapors adsorbed. The change in resistivity is due to adsorption of the chemical onto the metal layer. Because the chemical is adsorbed onto the metal layer, without reaction between the gold metal and the chemical, the adsorption is reversible by heating. (Col. 5, L. 13–15). The reversibility of the adsorption is a key difference between McNerney '562 and the present invention, which provides for an irreversible reaction between the switch material and the chemical to be detected. The present invention is also distinguished by the use of switch materials which can cause resistance to decrease, rather than increase, upon exposure to specific chemical components.

Justi, et al., U.S. Pat. No. 3,973,192, disclosed a device for providing an early detection of aerosol products of combustion originating at least partly from a polyvinyl chloride substance. The method consists of measuring the electrical resistance of a thin magnesium foil arranged to be exposed to the aerosol products of combustion. The magnesium foil is provided with a relatively deep corrosion layer of magnesium dichloride to accelerate the corrosion of the magnesium foil upon exposure to the aerosol products of combustion. This method is based on the aerosol products of combustion, which are formed on heating polyvinyl chloride substances to above 100° C. in a moist stream containing hydrochloric acid that can rapidly corrode the magnesium foil. Although this reaction is irreversible, magnesium is a rather reactive alkali earth metal, not a noble metal, and, therefore, cannot reactive selectively or function as a selective sensor. For example, magnesium will readily react with steam to form flammable hydrogen.

Takahama, et al., U.S. Pat. No. 4,224,280, disclosed a device for detecting carbon monoxide which exhibits a stepwise change in film current over a pre-selected range. The Takahama et al. device employs a plurality of semiconductor films. Three embodiments of the device are disclosed. A first embodiment consists of a stannic oxide ($SnO_2$) film formed on an insulating layer, with a second film layer of predominately platinum (Pt) formed on the first layer of stannic oxide. A second embodiment is identical, except that gold (Au) is added into the platinum layer in a gold-platinum alloy. The second layer is deposited with an average film thickness of 0.3 to 30 platinum atom layers, and the amount of gold ranges to 50 atomic percent of the platinum. A third embodiment contemplates that an electron donor of either antimony (Sb) or bismuth (Bi) is added to the first film layer, and an intermediate layer of stannic oxide having an electron acceptor selected from platinum, aluminum and boron is formed between the first and second films. The insulating film is silicon oxide ($SiO_2$). Electrodes connected to lead wires are used to provide a current in the device. A stepwise change in current results from exposure of the device to an atmosphere containing carbon monoxide. In this invention, a film of platinum or platinum and gold, having an atomic thickness that is narrow enough such that the film does not show a metallic, electrical conductivity, is formed on a film which essentially contains stannic oxide. (Col. 10, lines 31–36). Col. 6, lines 54–65 suggest that use of a gold second layer, i.e., one which is 100% gold, did not yield the characteristic stepwise current change. The use of gold as the second layer is, therefore, not suggested by the reference. Furthermore, FIGS. 7A, 7B and 8 of this patent show that the sensors do not show a very large response to carbon monoxide and that this response strongly depends on the operating temperatures of the device, which must be above 150° C. The inventors admit not to understanding the theoretical basis for the operation of this device. (Col. 6, lines 60–65). Although the inventors do not comment explicitly on the reversibility of their sensors, the response of heated stannic oxide devices is normally reversible.

U.S. Pat. No. 4,587,104 to Yannopoulos disclosed a gas combustible gas sensor which consists of an n-type semiconductor element. The semiconductor oxide is bismuth molybdate $Bi_2O_3 \cdot 3MoO_3$. Detection of the combustible gases is based upon the change of electrical conductivity of a thick film of the semiconductor oxide. The semiconductor sensor does not require a catalyst. The express teaching of the of the Yannopoulos patent is that semiconductor sensors are feasible without the presence of a noble metal catalyst, such as platinum, palladium and rhodium. The presence of a catalyst was previously necessary to yield conductivity changes in semiconductor oxide films which were large enough to measure. This reference suggests that it is not necessary, or even desirable, to employ a noble metal element in a gas detector device. The Yannopoulos patent is also based upon the reversible response of this sensor to hydrogen and carbon monoxide.

Komatsu, et al., U.S. Pat. No. 4,592,967, disclosed a gas sensor using mixed oxides, namely tin oxide, at least one lanthanide oxide, and at least one of the IVa group element oxides, e.g., titanium (Ti), zirconium (Zr), hafnium (Hf) or Thorium (Th) in a sintered piece covered with a porous layer of ceramic. The IVa oxide is present in the range of 0.01–20 mol % to keep electric conductance. The gas sensor is constantly heated to 300°–450° C. to enable rapid adsorption and desorption of the sensed gas on the sintered semiconductor. This type of device would clearly be unsuitable for applications where operation at ambient temperature is required and it is not based upon irreversible reactions of the sensor material.

Yoshioka, et al., U.S. Pat. No. 4,839,767, describes a device for detecting internal faults in an insulating gas-charged electrical apparatus. The device consists generally of a substrate, a pair of electrodes on the substrate and a thin metal film covering the electrodes and exposed to the substrate surface. The film produces fluorides with low conductivity upon reaction with a decomposed gas produced by internal faults of the electrical apparatus. The patent discloses that the film may be made of silver deposited on a substrate of $Al_2O_3$, with gold electrodes. The device is used to detect faults in apparatus charged with $SF_6$. $SF_6$ gas escaping through a fault decomposes to $SF_4$ or $SOF_2$, which produces HF upon reaction with trace moisture contained in the $SF_6$ gas. The silver film reacts with the HF to produce AgF which increases the resistance of the silver film. The patent discloses that an order-of-magnitude change in resistance occurs over many hours with a thin Ag film having thicknesses of between 100 Å–1000 Å. In one instance, there was a very rapid change in resistance, which required heating of the detection element to 80° C. The need for heating the detection element to obtain sufficiently rapid increases in resistance renders this arrangement unsuitable for a positive identification of chemical species in an ambient environment. In addition, the method disclosed by this patent is restricted to use in special environments, since silver passivates in the presence of oxygen and is not very selective in its reactivity.

The Koda, et al. patent, U.S. Pat. No. 4,938,928, disclosed a gas sensor designed for use at elevated temperatures, e.g., 300°– 400° C. The device consists of a semiconductor material selected to be specific for the gas to be detected. For example, metal oxide semiconductors of $SnO_2$, $In_2O_3$ and $Fe_2O_3$ are used to detect combustible and toxic gases; $BaSnO_3$, $LaNiO_3$ and NiO are used to detect oxygen; and ceramics such as $MgCr_2O_3$ or $TiO_2$ are useful for detecting humidity. Noble metals are used for the heat generating members to heat the semiconductor material to facilitate adsorption and desorption of chemical species onto the semiconductor material, resulting in fluctuations in resistance characteristics of the semiconductor. Again, this type of device is unsuitable for applications where operation at ambient temperature is required, and it is not based on irreversible reactions of the sensor material.

Bell, et al., U.S. Pat. No. 5,010,021, and its related U.S. Pat. No. 5,087,574, disclosed a method for detecting a fluid component within a fluid mixture. The method entails the selective adsorption of the component onto a conductive thin layer of material having a chemical affinity for the component, and observing the resulting change of electrical resistivity of the layer. The adsorption is reversible by heating to desorb the chemical species from the thin layer. The patents disclose the use of ozone to increase the dynamic range of the sensor.

With the exception of McNerney '562, Yoshioka '767 and Bell '021, the prior art references teach the use of non-noble metals and/or oxides as the conductive fuse element where the metal oxide's conductance changes measurably upon the adsorption of the particular chemical species to be detected. Typically, the surface adsorption and desorption reactions between the metal oxide and the chemical species occurs at elevated temperatures in the range of 300° C.–1000° C. The ability of the semiconductor material to desorb the chemical species is critical to the various functions of almost all of the prior art detection devices.

McNerney '562 teaches the use of a thin film of gold as a conductive element which becomes resistive upon exposure to mercury vapor. McNerney '562 expressly teaches that there is no reaction between the gold and the mercury vapor, rather the change in resistivity of the gold layer is due to an amalgamation of the mercury, which sequesters gold layer electrons resulting in their unavailability for electrical conduction. While the use of thin layer gold to detect mercury vapor is disclosed, the device and manner of use of the McNerney '562 device is distinct from that of the present invention. Specifically, the McNerney '562 device is designed to detect and measure minute traces of selected chemicals employing a metal non-reactive with the chemical species. The inert property of gold is utilized to assure that the adsorbed mercury vapor is capable of desorption upon heating of the detection device. As a consequence, the device does not act as an irreversible chemical sensor because the reaction is reversible.

A key difference between the present invention and the detection devices known in the art lies in the selective, irreversible bulk reaction of a chemical species with the chemical switch material in the present device. With the exception of Justi '192 and Yoshioka '767, the prior art discloses reversible surface reactions which induce electrical failure, but the present invention utilizes chemical activity within the bulk of the switch member to induce irreversible changes in the material properties. It is important, in the functioning of a switch, that the change be irreversible. Thus, the reversibility of the adsorption reaction at the surface of the sensors of the prior art sensors renders such devices inherently unsuitable for use as irreversible chemical switches. Furthermore, the nonselectivity, special atmospheres and operating conditions required for effective operation of the Justi '192 and Yoshioka '767 devices render them unsuitable for use as irreversible chemical switches to detect specific chemical components in the environment.

The device of the present invention is capable of undergoing a bulk reaction of the target chemical species at ambient temperature, as opposed to elevated temperatures required by prior art. This is advantageous because it has been found desirable to detect chemical species within the environment in which they may exist. For example, if chlorine gas should leak from a train tank car, a chlorine gas detector must be capable of operation within the temperature ranges in which the train tank car operates.

These devices have the potential to significantly advance emission detection and process control. For instance, in the emission detection arena, they have the unique advantages of being able to pinpoint leaks because they can be made sufficiently small to be placed at the source of the leak. Additional significant advantages of the inventive devices include low cost, low maintenance and no calibration. These chemical switches can find applications ranging from detecting leaks in individual tanks to tank farms to entire manufacturing facilities. Important chemical species with the potential to be detected include hazardous halogens, ammonia, hydrogen chloride, hydrogen fluoride, hydrogen sulfide and methane.

SUMMARY OF THE INVENTION

Accordingly, it is a principal object of the present invention to provide an irreversible chemical switch device which is irreversibly reactive to specific chemical species and exhibits a rapid, large change in electrical, optical, or other measurable property, upon reaction between the switch material and a specific chemical species. The reaction is manifested by a phase change in the switch material that, for example, can disrupt or enhance current flow through the switch material. The reaction is irreversible under the conditions of measurement. The present invention further provides a device which specifically detects at least one chemical component in the ambient environment. The device may be configured to detect more than one chemical species in a mixture or to specifically detect increasing concentrations of a particular chemical.

More specifically, the present invention is useful for specific detection of halogen gases such as chlorine. In accordance with one embodiment of the invention, the irreversible chemical switch is used to detect the presence of a chlorine gas leak by faulting or creating an electrically conductive pathway. The irreversible chemical switch has particular application for storage tanks and mobile tankers which routinely transport millions of gallons of highly toxic chlorine across the nation. The inventive irreversible chemical switch may also be configured, by selection of the appropriate noble metal, to detect the presence of chemicals as a warning device, to detect corrosion in pipelines or aircraft, to monitor vehicular emissions from combustion processes, or for any similar purpose where the selective detection of a chemical component is required.

DESCRIPTION OF PREFERRED EMBODIMENTS

Figure 1:
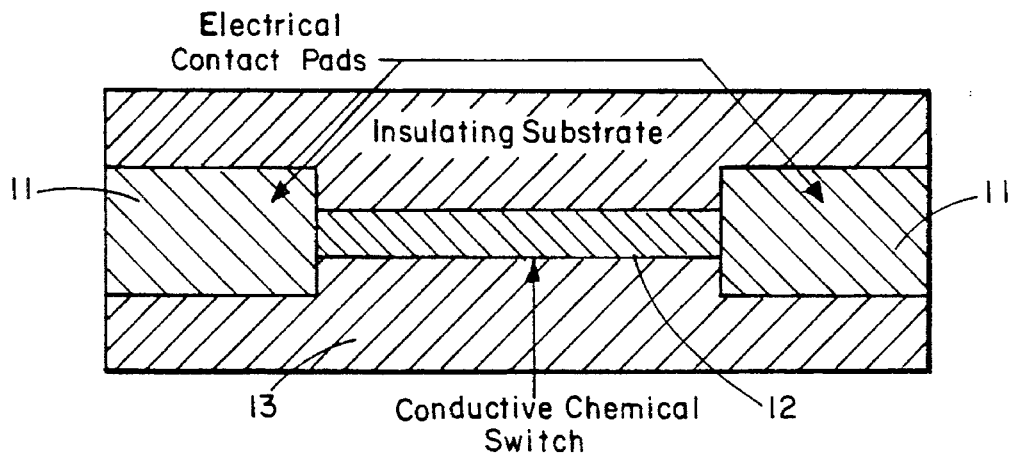
FIG. 1 is a top view schematically illustrating an irreversible chemical switch.

Certain thin or thick films can be engineered to undergo irreversible changes in properties, such as electrical, optical or the like, upon exposure to a sufficiently high concentration of a specific chemical species. In this respect, the film behaves effectively as an irreversible chemical switch for the detection of the desired chemical components. This film serves as the switch material.

The devices described in this present invention work on the basis of selective, irreversible chemical reactions between the film and one or more chemical components to be detected, at defective or reactive sites in the film. Defective and/or reactive regions in the film can be present naturally, such as grain boundaries, or can be introduced artificially, such as particularly thin or narrow regions for accelerated failure. The reaction sites are not limited to surface molecules, but occur throughout the bulk of the switch material as well.

As a target molecule adsorbs and/or absorbs to the switch film at a reaction site, a reaction occurs producing reaction products that have different properties relative to the starting switch film. For example, in the case of electrical properties, the reaction product can be either insulative or conductive relative to the starting switch film. As the degree of reaction increases with increasing concentration, there is an associated increase in the amount of insulative or conductive reaction products formed. Because reactive sites are found throughout the bulk of the film, insulative or conductive reaction products are integrated into the bulk, thus decreasing or increasing conductivity, respectively. For example, after a sufficient amount of insulative reaction products are formed, current flow is substantially decreased. This decrease can be detected and used as a switch to fault a circuit, or to initiate a warning or other sequence of events to maintain control of a dangerous chemical. Unlike an electrical fuse that fails due to physical breakage, the irreversible chemical switch undergoes a change in composition upon exposure to specific chemical components.

In order to detect a specific chemical component with a single switch it must be manufactured of a material that is highly selective to the desired component, yet substantially inert to all other chemicals that may be found in the ambient mixture. For example, for detection of toxic and corrosive chlorine, thin films of gold and gold alloyed with other noble metals have been found to be ideal switch materials. Except for surface reactions, which do not play a substantial role in the present invention, gold is inert to all of the common gases found in the work place and environment of the general public. However, gold does react readily with only the halogens, such as chlorine, to form bulk halides, such as gold chloride. Thus, gold can be used to accurately detect the presence of chlorine and other gold halide-forming halogens.

Irreversible chemical switch devices can be used not only as early warning devices and process control devices, but can signal long-term degradation of construction materials. For example, to detect long-term degradation or corrosion of a pipe carrying natural gas containing corrosive hydrogen sulfide, the switch material can be designed to fail after long-term exposure to the natural gas. This design is achieved by manufacturing the switch of a material identical to or simulating the interior pipe material. The device is then exposed to the natural gas and upon failure, indicates that the bulk pipe materials have degraded, although not yet to a failure point. For this important application, the detection is rapid in the sense that the chemical switch is engineered to activate well before the pipe materials have experienced severe corrosion. Such application of an irreversible chemical switch for reliable detection of pipe corrosion or degradation before failure has important benefits for waste, contamination and safety issues.

The reaction mechanism at the reaction sites is dependent on the material used for the switch and the reactant chemical species, but in general can be characterized as a phase change within the bulk of the switch material due to an irreversible chemical reaction, such as alloying or compound formation. For electrical resistance measurements, these bulk reactions occur to produce insulative or conductive products by irreversible reaction mechanisms. Irreversible reactions involving changes in electrical properties offer a very large dynamic range, approaching changes as large as $10^{20}$. Such large electrical changes can be used to differentiate the presence of chemical species that cause bulk reactions from those that simply adsorb onto the surface.

Because the device fuse action depends on the number of reactions which create new products, the device reactivity can be crafted by careful engineering of the properties of the bulk material. For example, if the film is made thicker, it takes more time for the irreversible reactions to permeate the bulk of the film. Consequently, it takes a higher concentration of chemical species to generate the same response in a given time. The number of reaction sites within the bulk can also affect the reactivity of the fuse. For example, the concentration of desired intrinsic and extrinsic defects, such as bulk defects and grain homogeneity, which serve as reaction sites, can be controlled by the proper choice of the conditions and materials used to fabricate the switches.

A variety of electrically insulating fuse substrates can be used to optimize switch performance, because the substrate influences the grain structure of the deposited switch material. Substrate materials include $SiO_2/Si$, $Al_2O_3$, mica, graphite and polyimide polymers. These substrates exhibit a broad range of compositions and microstructures to control switch reactivity. $SiO_2$ has small, compact grain boundaries and is ideal for further device development using semiconductor processing and device technology. $Al_2O_3$ can be obtained with a variety of surface roughnesses that tend to have a large distribution of grain sizes and associated voids that promote strong adhesion. Mica is the substrate of choice to obtain highly crystalline films having a minimum number of defects, and polyimide polymers are flexible, inexpensive materials that are thermally stable and have been used commercially as substrates for chemical sensors.

Switch reactivity can be further manipulated with chemical modification. Additives can be deposited either simultaneously or serially during switch deposition to produce desirable switch performance, such as enhancing and/or controlling sensitivity and/or selectivity. For example, gold film reactivity to chlorine may be enhanced by adding silver, which is more reactive to chlorine, or by adding chromium, which suppresses gold's reactivity. Furthermore, switch films can be stacked to produce any desired combination of switch performance characteristics.

However, in addition to its effects on the bulk properties of the film, chemical modification can also affect how well the switch material adheres to the substrate. Adherence to the substrate can affect switch reactivity. Irreversible chemical switches that rely on poorly adhering films, such as gold, often require "adhesive" metals to be deposited between the substrate and the gold to provide the adhesion necessary for non-sensing functions such as electrical connections. However, as explained above, these same metals that are used as adhesives can adversely affect the sensor properties. In the case of gold film sensors, using chromium as the adhesive layer, repeated or continuous exposure of the fuse to elevated temperatures can cause the chromium to migrate into the gold film, resulting in loss of sensitivity or failure. This problem can be circumvented by depositing adhesive materials only on those regions where they are required, such as electrical connections, and not on the sensing portion of the device. To eliminate adherence of the sensing portion of the device, the switch material can be deposited over an air gap so that there is no physical contact between the switch material and the substrate.

Alternatively, substantial enhancement in the adhesive forces between a film and an underlying substrate can be obtained by promoting the penetration of the film into defects in the substrate. For example, gold adhesion to silica substrates can be improved by annealing the gold/silica structure at temperatures above 600° C. for more than 15 minutes, which causes the gold to intrude into the amorphous silica layer defects.

It should be pointed out that other approaches to measure switch response, such as an optical approach using reflected or transmitted light, need not require the relatively good adhesion needed for electrical measurement.

By combining several of the factors contributing to the reactivity of the switch material, devices of various sensitivities can be created. The following embodiments are intended to serve as examples of the application of the invention herein described, and are not to be considered limiting.

PREFERRED EMBODIMENT #1

FIG. 1 shows the top view of a basic irreversible chemical switch 10 for the detection of chlorine. Contact pads 11, connected to a switch material 12, are deposited on a substrate 13. For detection of chlorine, the contact pads 11 and switch material 12 are made of a thin (80–500 Å) and narrow (<100μ) film of gold. The substrate 13 may be made of alumina, silica or silicon nitride.

PREFERRED EMBODIMENT #2

Figure 2:
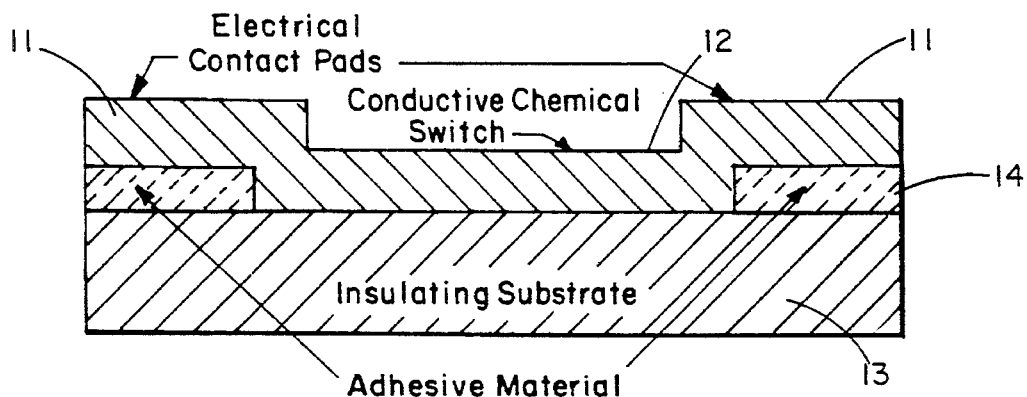
FIG. 2 is a cross-sectional view illustrating an irreversible chemical switch.

FIG. 2 shows a cross-section of an irreversible chemical switch for electrical resistance measurements having increased functionality by depositing adhesive material 14 in strategic locations under the contact pads 11. For detection of chlorine, contact pads 11 can be made of gold having a thickness of 1,000–10,000 Å and the switch material 12 is made of a gold film having a thickness of 80–1,000 Å. The switch material 12 is less than 100μ wide and the substrate 13 is selected from the group consisting of alumina, silica or silicon nitride. The adhesive material 14 is a thin film selected from the group of chromium, titanium or aluminum.

PREFERRED EMBODIMENT #3

Figure 3:
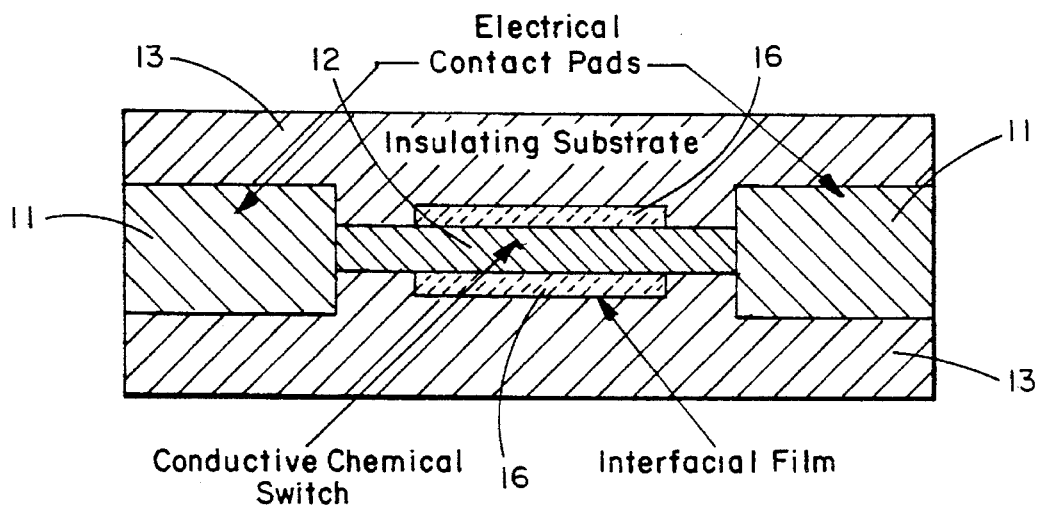
FIG. 3 is a top view schematically illustrating an irreversible chemical switch utilizing an interfacial film to achieve poor adhesion between the switch material and a dielectric substrate.
Figure 4:
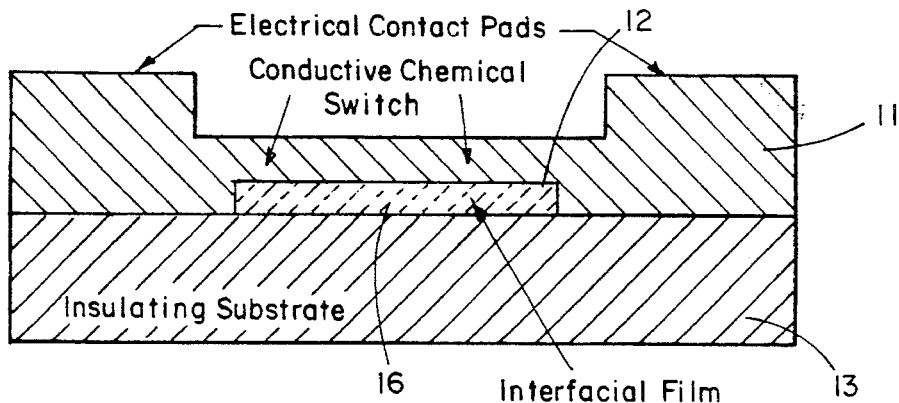
FIG. 4 is a cross-section schematically illustrating an irreversible chemical switch utilizing an interfacial film to achieve poor adhesion between the switch material and the dielectric substrate.

FIGS. 3 and 4 illustrate an irreversible chemical switch device for electrical resistance measurements with the switch material 12 deposited on an interfacial film 16 which has been deposited on a substrate 13. The contact pads 11 exhibit good adhesion to the substrate 13, but the switch material 12 shows poor adhesion to the interfacial film 16. For detection of chlorine contact pads 11 can be made of gold having a thickness of 1,000–10,000 Å and the switch material 12 is made of a gold film having a thickness of 80–1,000 Å. The switch material 12 is less than 100μ wide and the substrate 13 is selected from the group consisting of alumina, silica or silicon nitride. The interfacial film can be a polymer such as polyimide.

PREFERRED EMBODIMENT #4

Figure 5:
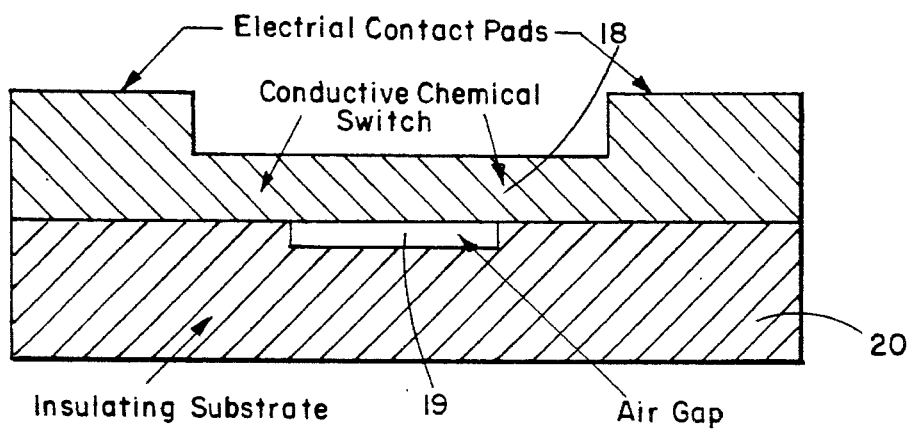
FIG. 5 is a cross-section schematically illustrating an irreversible chemical switch utilizing an air gap to achieve poor adhesion between the switch material and the dielectric substrate.

FIG. 5 is a cross-section of an irreversible chemical switch device for electrical resistance measurements based upon suspending the switch material 18 across an air gap 19 on a substrate 20. The switch material 18 has no adhesion to the substrate across the air gap 19 and, hence, provides an optimum arrangement for rapid device failure due to selective chemical reactions. The air gap can be created by depositing the switch region on a sacrificial region of the substrate that can be removed after deposition.

PREFERRED EMBODIMENT #5

Figure 6:
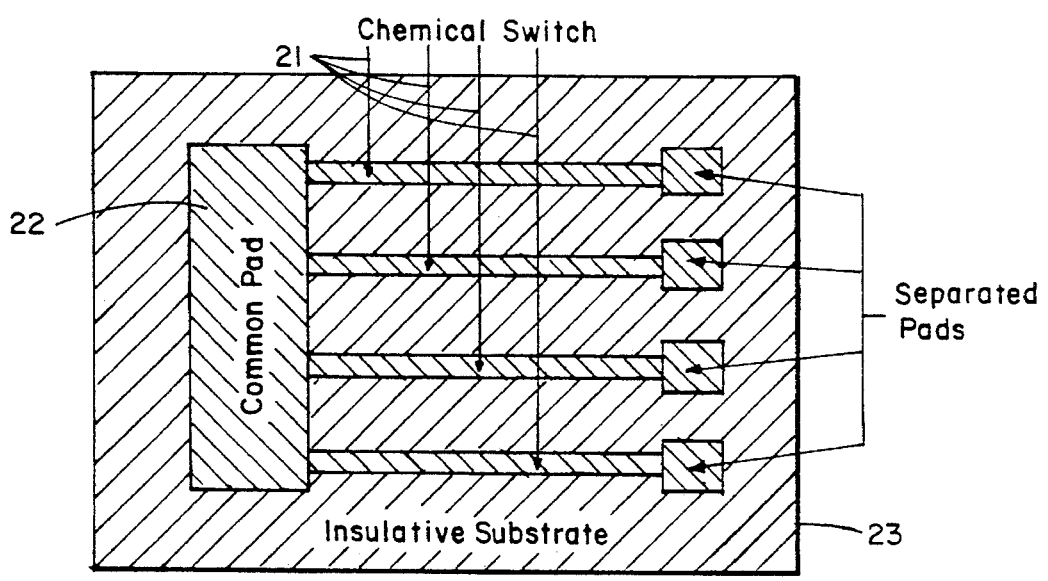
FIG. 6 is a top view schematically illustrating a multi-element irreversible chemical switch design which improves reliability of the device by requiring irreversible reaction of multiple switches in order to signal the presence of a specific chemical.

FIG. 6 illustrates a multi-element irreversible chemical switch designed to achieve improved reliability by responding only to multiple switch element signals. For electrical resistance measurements, switch materials 21 can be of equal width, tied to a common electrical connecting pad 22 and deposited on a common substrate 23.

PREFERRED EMBODIMENT #6

Figure 7:
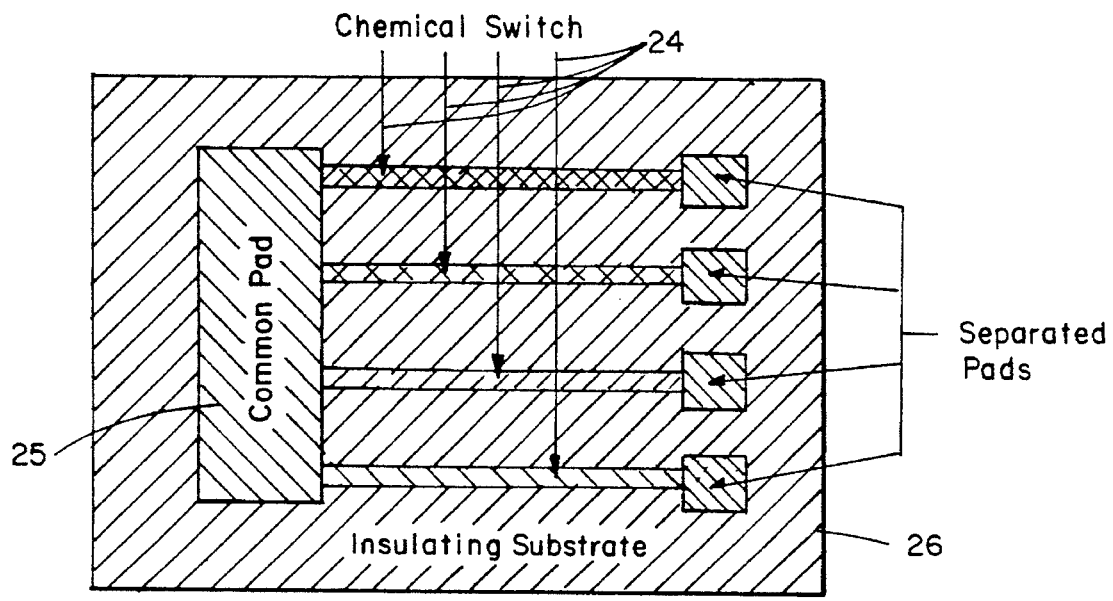
FIG. 7 is a top view schematically illustrating an irreversible chemical switch array designed to detect the concentration of a specific chemical by utilizing switches of the same material but of different dimensions, which exhibit measurable properly changes at progressively higher concentrations of the specific chemical.

FIG. 7 illustrates a multi-element irreversible chemical switch designed to detect the concentration of a particular chemical component by exhibiting failure at progressively higher concentrations of the component. A plurality of switch elements 24, made of the same material but of different thicknesses, are deposited onto an underlying substrate. The response of each of the plurality of switch elements 24 is indicative of the concentration of the particular chemical component. The switch materials 24 are tied to a common electrical connecting pad 25 and deposited on a common substrate 26. This concentration-level design can be used to assess the maximum concentration of a chemical component to which the switch array has been exposed.

PREFERRED EMBODIMENT #7

Figure 8:
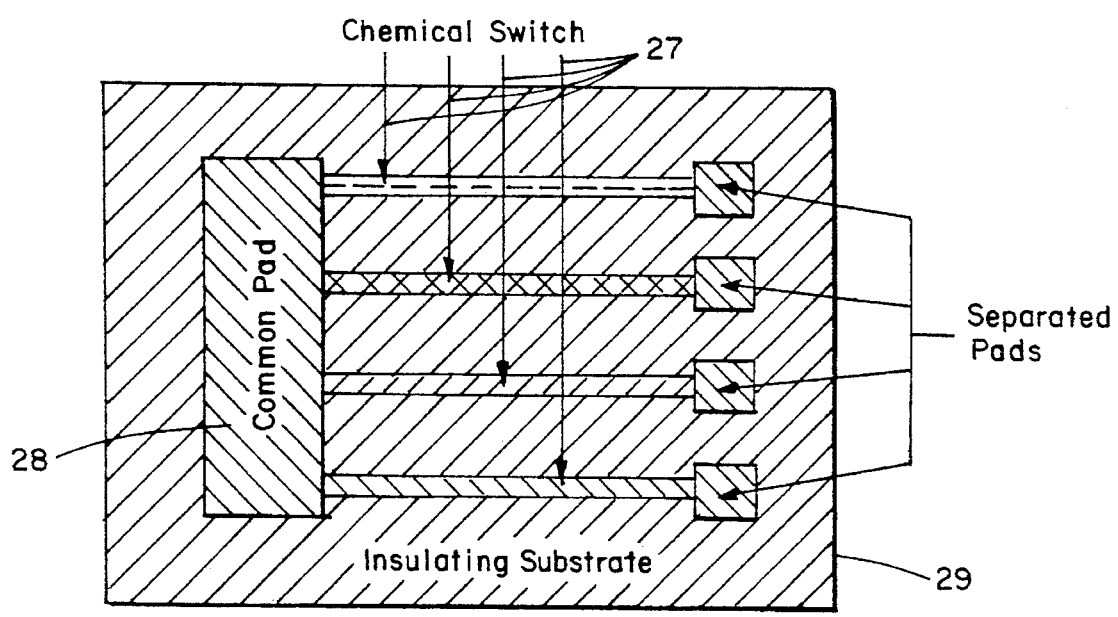
FIG. 8 is a top view schematically illustrating an irreversible chemical switch array designed to detect the presence of more than one chemical by utilizing switches composed of different materials which are selectively reactive with different chemicals.

FIG. 8 illustrates a multi-element irreversible chemical switch designed to detect more than one chemical component within a single switch-element array. A plurality of switch elements 27 are composed of different materials which are discretely or differentially reactive to different chemical components. For electrical resistance measurements, each of the plurality of switch elements 27 are tied to a common electrical connecting pad 28 and deposited on a common substrate 29. This multi-component design can be used to evaluate the proportion of the different constituents in a mixture.

PREFERRED EMBODIMENT #8

A basic irreversible chemical switch is designed for the detection of chlorine gas. Contact pads, connected to a switch material, are deposited on an insulating substrate. The contact pads and switch material are made of gold films which are 5,000 Å and 150 Å thick, respectively. The switch material is 100 microns wide, and the substrate is silica or silicon. Device exposure to approximately 1% chlorine (by volume) in air resulted in a resistance increase of seven orders of magnitude in six seconds.

Ultra thin films of about 20 Å–80 Å in thickness can be employed as highly sensitive, rapid reactive switch elements for extremely low concentrations of a chemical, such as chlorine. Conversely, a thick film of between 1,000 Å to 100,000 Å can be used for switches where a large volume of high concentrations of a chemical, such as chlorine, may be encountered.

While the invention has been fully described with reference to certain preferred embodiments thereof, those skilled in the art will understand and appreciate that changes may be made and still fall within the spirit and scope of the present invention. For example, alternative measurement methods, substrate materials, switch materials and dimensions, switch arrangements, or methods of adhering the switch material to the substrate may be employed.

What is claimed is:

1. A method for detecting the presence of a chemical constituent in an open ambient environment, comprising the steps of:
    A. providing a switch element made of a noble metal or noble metal alloy material which is substantially inert, unreactive to primary constituents in the open ambient environment in which the switch element resides, but selectively and irreversibly reactive only with a chemical constituent to be detected in an open ambient environment, said material being selected and arranged so as to provide a binary electrical response to said chemical reaction;
    B. exposing said switch element to the open ambient environment, thereby causing a reaction between said switch element and the chemical constituent, if present in the open ambient environment; and
    C. measuring said electrical response of the switch element to determine the presence of the chemical constituent.

2. The method of claim 1, wherein said step of exposing said switch element further comprises the step of reacting said switch element and the chemical constituent by at least one of a surface, interfacial or bulk reaction.

3. The method of claim 1, wherein said step of exposing said switch element further comprises the step of creating at least one chemical reaction selected from the group consisting of an amalgamation, corrosion, acid-base, oxidation-reduction or precipitation reaction between the chemical constituent and the switch element.

4. The method of claim 1, wherein said step of exposing said switch element to an environment further comprises exposing said switch element to an environment containing at least one of a halogen or hydrogen halides.

5. The method of claim 1, wherein said step of determining the presence of the chemical constituent further comprises measuring a change in electrical resistance of the switch element of at least one order of magnitude relative to unreacted switch element.

6. The method of claim 1, wherein said step of providing a switch element further comprises the step of providing a switch element made of a substantially inert material selected from the group of gold and gold alloys.

7. A method for detecting a chemical constituent, comprising the steps of:
    A. establishing an electrical current in at least one switch element associated with a substrate;
    B. exposing said at least one switch element to an open ambient environment suspected of containing a detectable chemical constituent, said at least one switch element comprising substantially inert noble metal or noble metal alloy material which is unreactive to primary constituents of the open ambient environment, but selectively reactive only to the detectable chemical constituent, said material being selected and arranged so as to provide a binary electrical response to said chemical reaction;
    C. selectively reacting the chemical constituent with said substantially inert material of said at least one switch element by at least one of surface, interfacial or bulk reaction; and
    D. monitoring said at least one switch element for said binary electrical response due to reaction of the substantially inert material of said at least one switch element with the chemical constituent, said response being indicated by an irreversible phase change in the switch element.

8. The method of claim 7, wherein said step of reacting the chemical constituent further comprises the step of creating at least one irreversible reaction selected from the group consisting of amalgamation, corrosion, acid-base, oxidation-reduction or precipitation reaction between the chemical constituent and the switch material.

9. The method of claim 7, wherein said step of exposing said at least one switch element to an environment further comprises exposing said at least one switch element to an environment containing at least one of a halogen or hydrogen halides.

10. The method of claim 7, wherein said step of providing at least one switch element further comprises the step of providing a switch element made of a substantially inert material selected from the group of gold and gold alloys.

* * * * *

UNITED STATES PATENT AND TRADEMARK OFFICE
CERTIFICATE OF CORRECTION

PATENT NO. : 5,466,605
DATED : February 14, 1995
INVENTOR(S) : William Glaunsinger, et al.

It is certified that error appears in the above-indentified patent and that said Letters Patent is hereby corrected as shown below:

Column 7, Line 5, after "measurable ", delete "properly" and insert --property--.

Signed and Sealed this

Twenty-third Day of April, 1996

Attest:

BRUCE LEHMAN

Attesting Officer

Commissioner of Patents and Trademarks